(12) United States Patent
Johnson et al.

(10) Patent No.: US 10,925,644 B2
(45) Date of Patent: *Feb. 23, 2021

(54) IMPLANTABLE FLUID DELIVERY DEVICES, SYSTEMS, AND METHODS

(71) Applicant: PALO ALTO RESEARCH CENTER INCORPORATED, Palo Alto, CA (US)

(72) Inventors: David Mathew Johnson, San Francisco, CA (US); Scott A. Uhland, San Jose, CA (US); Ramkumar Abhishek, Mountain View, CA (US); Robert Thomas Krivacic, San Jose, CA (US); Martin Sheridan, Redwood City, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 482 days.

This patent is subject to a terminal disclaimer.

(21) Appl. No.: 15/727,766

(22) Filed: Oct. 9, 2017

(65) Prior Publication Data
US 2018/0028228 A1 Feb. 1, 2018

Related U.S. Application Data

(62) Division of application No. 14/448,087, filed on Jul. 31, 2014, now Pat. No. 9,801,660.

(51) Int. Cl.
*A61B 17/43* (2006.01)
*A61M 31/00* (2006.01)
(Continued)

(52) U.S. Cl.
CPC ............... *A61B 17/43* (2013.01); *A61D 7/00* (2013.01); *A61M 31/002* (2013.01); *A61B 17/435* (2013.01)

(58) Field of Classification Search
CPC ........ A61B 17/425; A61B 17/43; A61D 7/00; A61D 19/02
(Continued)

(56) References Cited

U.S. PATENT DOCUMENTS 3,822,702 A * 7/1974 Bolduc ................. A61B 17/42
128/831
4,304,232 A 12/1981 Michaels
(Continued)

FOREIGN PATENT DOCUMENTS

DE 4130843 A1 3/1993
WO 94/01165 A1 1/1994
(Continued)

OTHER PUBLICATIONS

Boehmer et al., "Effects of Temperature of Consumed Water on Rumen Temperature of Beef Cows," Oklahoma Agricultural Experiment Station, 2009, 4 pages.
(Continued)

*Primary Examiner* — John P Lacyk
(74) *Attorney, Agent, or Firm* — Mueting Raasch Group (57) ABSTRACT

Devices, systems, and methods for delivering fluid are provided. Devices include a housing configured for intravaginal deployment and retention, at least one reservoir configured to contain a fluid, and a fluid dispensing mechanism configured to dispense the fluid past the cervix and to the uterus of the subject. Methods include intravaginally deploying and retaining a device in the subject, and dispensing the fluid from the device such that the fluid is driven past the cervix to the uterus of the subject.

17 Claims, 9 Drawing Sheets

(51) Int. Cl.
*A61D 7/00* (2006.01)
*A61B 17/435* (2006.01)

(58) Field of Classification Search
USPC .................................................. 600/33–35
See application file for complete search history.

(56) References Cited

U.S. PATENT DOCUMENTS

| | | |
|---|---|---|
| 4,308,867 A | 1/1982 | Roseman et al. |
| 4,402,695 A | 9/1983 | Wong |
| 4,687,423 A | 8/1987 | Maget et al. |
| 4,886,514 A | 12/1989 | Maget |
| 4,892,778 A | 1/1990 | Theeuwes et al. |
| 4,902,278 A | 2/1990 | Maget et al. |
| 5,002,540 A | 3/1991 | Brodman et al. |
| 5,062,834 A | 11/1991 | Gross et al. |
| 5,090,963 A | 2/1992 | Gross et al. |
| 5,112,614 A | 6/1992 | Magruder et al. |
| 5,135,499 A | 8/1992 | Tafani et al. |
| 5,162,116 A | 9/1992 | Shepherd et al. |
| 5,318,557 A | 6/1994 | Gross |
| 5,354,264 A | 10/1994 | Bae et al. |
| 5,415,629 A | 5/1995 | Henley |
| 5,522,804 A | 6/1996 | Lynn |
| 5,593,552 A | 1/1997 | Joshi et al. |
| 5,780,058 A | 7/1998 | Wong et al. |
| 5,816,248 A | 10/1998 | Anderson et al. |
| 5,928,195 A | 7/1999 | Malamud et al. |
| 5,951,538 A | 9/1999 | Joshi et al. |
| 6,030,375 A | 2/2000 | Anderson et al. |
| 6,086,909 A | 7/2000 | Harrison et al. |
| 6,139,538 A | 10/2000 | Houghton et al. |
| 6,183,434 B1 | 2/2001 | Eppstein |
| 6,322,532 B1 | 11/2001 | D'Sa et al. |
| 6,352,524 B1 | 3/2002 | Bunt |
| 6,423,039 B1 | 7/2002 | Rathbone et al. |
| 6,444,224 B1 | 9/2002 | Rathbone et al. |
| 6,450,991 B1 | 9/2002 | Bunt et al. |
| 6,532,386 B2 | 3/2003 | Sun et al. |
| 6,591,133 B1 | 7/2003 | Joshi |
| 6,638,246 B1 | 10/2003 | Naimark et al. |
| 6,743,211 B1 | 6/2004 | Prausnitz et al. |
| 6,756,053 B2 | 6/2004 | Zhang et al. |
| 6,776,164 B2 | 8/2004 | Bunt et al. |
| 6,805,877 B2 | 10/2004 | Massara et al. |
| 6,835,392 B2 | 12/2004 | Hsu et al. |
| 6,962,579 B2 | 11/2005 | Jellie |
| 6,978,172 B2 | 12/2005 | Mori et al. |
| 7,004,171 B2 | 2/2006 | Benita et al. |
| 7,083,575 B1 | 8/2006 | Claycomb et al. |
| 7,083,590 B1 | 8/2006 | Bunt et al. |
| 7,486,989 B2 | 2/2009 | Sun et al. |
| 7,497,855 B2 | 3/2009 | Ausiello et al. |
| 7,732,408 B2 | 6/2010 | Josephson et al. |
| 9,297,083 B2 | 3/2016 | Abhishek et al. |
| 9,801,660 B2 * | 10/2017 | Johnson .................. A61D 7/00 |
| 2002/0010414 A1 | 1/2002 | Coston et al. |
| 2002/0045883 A1 | 4/2002 | Jellie et al. |
| 2002/0156394 A1 | 10/2002 | Mehrotra |
| 2003/0018295 A1 | 1/2003 | Henley et al. |
| 2003/0130558 A1 | 7/2003 | Massara et al. |
| 2003/0219472 A1 | 11/2003 | Paulelli et al. |
| 2004/0059388 A1 | 3/2004 | Herbst et al. |
| 2004/0082937 A1 | 4/2004 | Ausiello et al. |
| 2004/0087893 A1 | 5/2004 | Kwon |
| 2004/0219192 A1 | 11/2004 | Horstmann et al. |
| 2005/0000514 A1 | 1/2005 | Sullivan et al. |
| 2005/0054969 A1 | 3/2005 | Hoff et al. |
| 2005/0124875 A1 | 6/2005 | Kawano et al. |
| 2005/0244502 A1 | 11/2005 | Mathias et al. |
| 2005/0267440 A1 | 12/2005 | Herman et al. |
| 2006/0024358 A1 | 2/2006 | Santini et al. |
| 2006/0184092 A1 | 8/2006 | Atanasoska et al. |
| 2007/0038181 A1 | 2/2007 | Melamud et al. |
| 2007/0173711 A1 | 7/2007 | Shah et al. |
| 2007/0225634 A1 | 9/2007 | Ferren et al. |
| 2007/0269385 A1 | 11/2007 | Yun et al. |
| 2008/0004564 A1 | 1/2008 | Smith |
| 2008/0004596 A1 | 1/2008 | Yun et al. |
| 2008/0171950 A1 | 7/2008 | Franco |
| 2008/0262412 A1 | 10/2008 | Atanasoska et al. |
| 2008/0269666 A1 | 10/2008 | Wang et al. |
| 2009/0131737 A1 | 5/2009 | Ferren et al. |
| 2009/0171315 A1 | 7/2009 | Versi |
| 2009/0281528 A1 | 11/2009 | Grovender |
| 2009/0306633 A1 | 12/2009 | Trovato et al. |
| 2009/0308752 A1 | 12/2009 | Evans |
| 2011/0087155 A1 | 4/2011 | Uhland et al. |
| 2011/0087192 A1 | 4/2011 | Uhland et al. |
| 2011/0087195 A1 | 4/2011 | Uhland et al. |
| 2011/0092906 A1 | 4/2011 | Boettger |
| 2012/0238912 A1 | 9/2012 | Rajkondawar et al. |
| 2013/0211372 A1 | 8/2013 | Rosenshein |
| 2014/0088345 A1 | 3/2014 | Uhland et al. |
| 2014/0088346 A1 | 3/2014 | Uhland et al. |
| 2014/0088486 A1 | 3/2014 | Uhland et al. |
| 2014/0200553 A1 | 7/2014 | Johnson et al. |
| 2015/0126968 A1 | 5/2015 | Abhishek et al. |

FOREIGN PATENT DOCUMENTS

| | | |
|---|---|---|
| WO | 94/18952 A1 | 9/1994 |
| WO | 97/41831 A1 | 11/1997 |
| WO | 01/12101 A1 | 2/2001 |
| WO | 2005/056708 A2 | 6/2005 |
| WO | 2005/089728 A2 | 9/2005 |
| WO | 2007/041119 A1 | 4/2007 |
| WO | 2007/047811 A2 | 4/2007 |
| WO | 2007/140416 A2 | 12/2007 |
| WO | 2009/081411 A2 | 7/2009 |
| WO | 2010/048478 A2 | 4/2010 |

OTHER PUBLICATIONS

Boehmer, "Ruminal Temperature for Identification and Prediction of Estrus in Beef Cows," 2012, Thesis.
Heckman et al., "Estrous Cycle Patterns in Cattle Monitored by Electrical Resistance and Milk Progesterone," 1979, J. Dairy Sci., 62:64-68.
de Mol et al., "Application of Fuzzy Logic in Automated Cow Status Monitoring," 2001, J. Dairy Sci., 84:400-410.
O'Connor, "Heat Detection and Timing of Insemination for Cattle," 1993, Pennsylvania State University, Extension Circular 402.
Piccione et al., "Daily and Estrous Rhythmicity of Body Temperature in Domestic Cattle," 2003, BioMed Central, (8 pages).
Cooper-Prado et al., "Relationship of Ruminal Temperature with Parturition and Estrus of Beef Cows," 2011, J. Anim. Sci., 89:1020-1027.
http://ww.beaconhd.com.au/heatseeker.html, Beacon Heat Detectors, accessed on Feb. 27, 2014.
http://www.twilcanada.com/estrus-detector.php, Estrus Detector, accessed on Feb. 27, 2014.
http://www.cowchips.net/, How HeatWatch II Works, accessed on Feb. 27, 2014.
Bridges, et al., "Timed-Artificial Insemination in Beef Cows: What are the Options?," Purdue University Cooperative Extension Service, West Lafayette, IN (Rev Mar. 2008).
Fatakdawala, Hussain et al., "Hydrogen peroxide mediated transvaginal drug delivery," International Journal of Pharmaceutics 409 (2011) 121-127.
Hashimoto et al., "Oxidative stress induces gastric epithelial permeability through claudin-3." Biochemical and Biophysical Research Communications (2008), vol. 376, pp. 154-157.
Kadajji, et al., "Water Soluble Polymers for Pharmaceutical Applications." Polymers (2011), vol. 3, pp. 1972-2009.
Sáfilho, O. G. et al., "Fixed-time artificial insemination with estradiol and progesterone for Bos indicus cows II: Strategies and factors affecting fertility," Science Direct, Theriogenology 72 (2009) 210-218.

(56) References Cited

OTHER PUBLICATIONS

Seth, et al., "Probiotics ameliorate the hydrogen peroxide-induced epithelial barrier disruption by a PKC-and MAP kinase-dependent mechanism," Am J Physiol Gastrointest Liver Physiol (2008), vol. 294, pp. G1060-G1069. Retrieved from http://www.ajpgi.org on Jul. 28, 2009.

* cited by examiner

IMPLANTABLE FLUID DELIVERY DEVICES, SYSTEMS, AND METHODS

CROSS-REFERENCE TO RELATED APPLICATIONS

This application is a divisional of U.S. application Ser. No. 14/448,087, filed Jul. 31, 2014, which is incorporated herein by reference in its entirety.

TECHNICAL FIELD

The present disclosure relates generally to implantable medical devices, and more particularly to devices, systems, and methods for delivering fluid to the uterus of a subject.

BACKGROUND

Medical devices may be used to deliver fluids (e.g., drugs or other fluids) to a patient or subject. Certain devices may be configured to be implanted at a patient site and deliver a fluid thereto. For example, intrauterine devices may be used to deliver fluids directly to the uterus of a patient, such as in an in vitro fertilization (IVF) procedure to increase the likelihood of pregnancy and/or to control certain aspects of a pregnancy.

However, devices that can be deployed in the uterus of a subject must have a particular size, shape, and design, which may be difficult to achieve for certain devices and/or fluid payloads. So while devices that are implantable in the uterus can dispense fluid, such as semen in an IVF procedure, directly to the surrounding tissue with a high probability of fluid delivery to the uterus, it is not feasible to design every fluid delivery device to be implanted in the uterus.

Intravaginal devices have fewer design limitations relating to the deployment site than intrauterine devices; however, if the device can only be placed within the vaginal cavity, dispensing a fluid to the uterus, such as semen in an IVF procedure, can be considerably more difficult. Accordingly, there is a need for improved intravaginal devices, systems, and methods that provide fluid delivery to the uterus of a subject.

SUMMARY

In one aspect, implantable fluid delivery devices are provided, including a housing configured for intravaginal deployment and retention in a subject, at least one reservoir associated with the housing and configured to contain a fluid, and a fluid dispensing mechanism disposed within the housing and configured to dispense the fluid from the at least one reservoir past the cervix and to the uterus of the subject.

In another aspect, implantable fluid delivery systems are provided, including a device having a housing configured for intravaginal deployment and retention in a subject and a fluid dispensing mechanism disposed within the housing; and a capsule containing a fluid to be delivered to the subject, the capsule being configured to be inserted past the cervix of the subject prior to deployment of the device, wherein the fluid dispensing mechanism includes an ultrasonic element configured to generate an ultrasonic wave effective to rupture the capsule and release the fluid to the uterus of the subject.

In yet another aspect, methods of delivering fluid to a subject are provided, including intravaginally deploying and retaining a device in the subject, the device including at least one reservoir containing a fluid and a fluid dispensing mechanism; and dispensing the fluid from the device such that the fluid is driven past the cervix to the uterus of the subject.

In still yet another aspect, methods of delivering fluid to a subject are provided, including inserting a capsule containing a fluid to be delivered to the subject past the cervix of the subject; thereafter intravaginally deploying a device in the subject, the device including a fluid dispensing mechanism, which includes an ultrasonic element; and generating an ultrasonic wave, via the ultrasonic element, effective to rupture the capsule and release the fluid to the uterus of the subject.

DETAILED DESCRIPTION

The devices, systems, and methods described herein meet one or more of the above-stated needed by provided implantable fluid delivery to the uterus of a subject. In certain embodiments, an intravaginal device is provided that is capable of delivering a fluid past the cervix and to the uterus of a subject.

Such devices may be particularly useful in animals, such as cattle, where the IVF procedure has to be performed by a skilled professional and is a time-consuming, costly, and intensive procedure for each animal. The devices, systems, and methods disclosed herein increase the likelihood of success of each IVF procedure by increasing the precision of the fluid delivery. As such, the valuable sperm and the time commitment from these professionals may be most effectively and efficiently used.

Implantable Fluid Delivery Devices and Systems

In one aspect, implantable fluid delivery devices and systems are provided, which allow for the controlled dispense or release of one or more fluids to the uterus of a subject. In embodiments, the release or dispense is temporally controlled, such that the fluid substance reaches the uterus at a selected time.

Figure 1A:
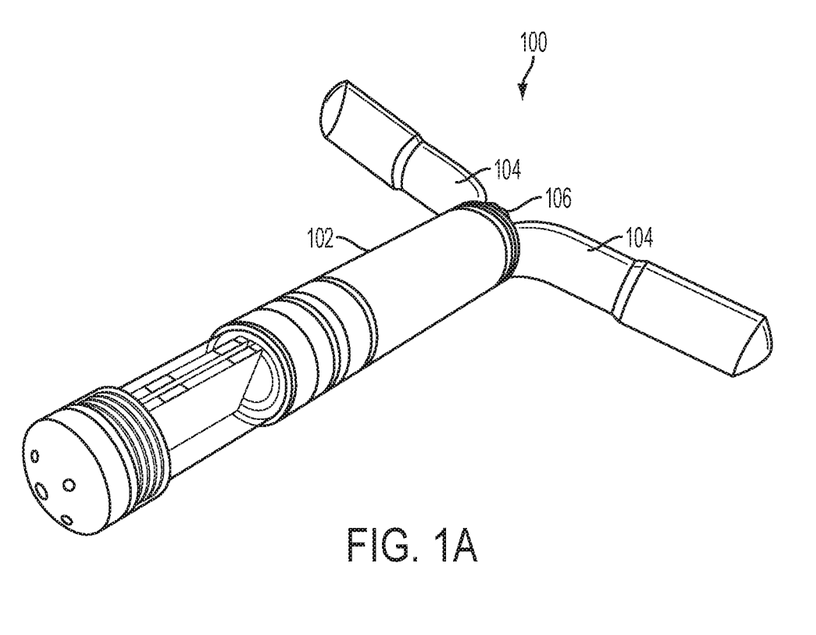
FIG. 1A is a perspective view of an implantable fluid delivery device.
Figure 1B:
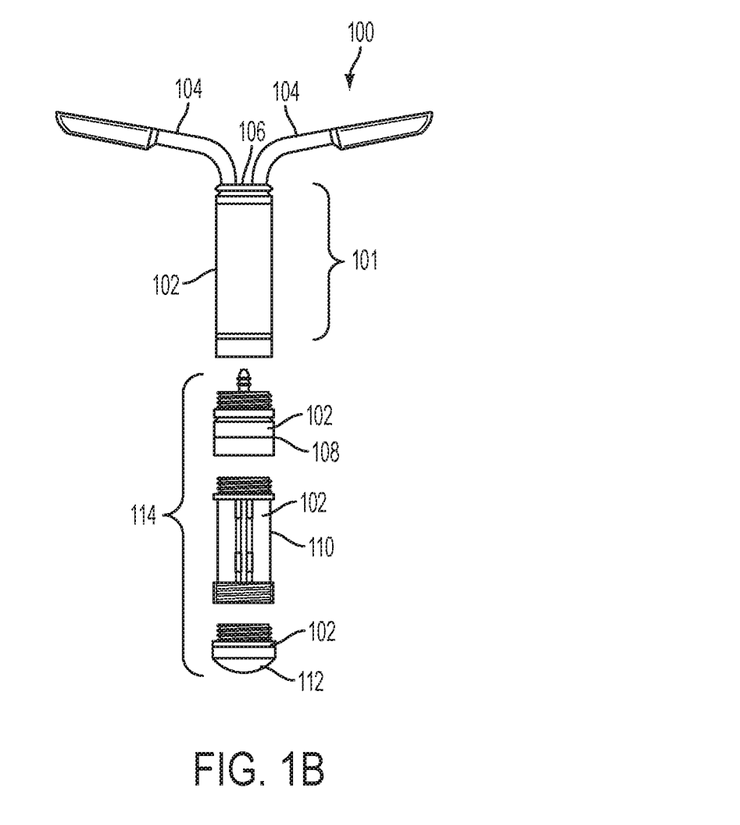
FIG. 1B is an exploded view of the implantable fluid delivery device of FIG. 1A.

In one embodiment, as shown in FIGS. 1A and 1B, an implantable fluid delivery device 100 includes a housing 102 configured for intravaginal deployment and retention in a subject. For example, the housing 102 of the device 100 may be sized and shaped for intravaginal deployment and retention in the subject. In one embodiment, the device 100 includes one or more retention features 104, for retaining the device intravaginally upon deployment.

For example, as shown in FIGS. 1A and 1B, depending on the fluid dispensing mechanism, and the power and actuation needs of the device, the device 100 may include a control system 114 that includes one or more of a power source 112, a microcontroller 110, and an actuation mechanism 108. In addition, the device 100 may include a fluid dispensing system 101, which alone or in combination with the control system, operates to dispense or release a fluid to the subject. The device 100 may also include a fluid dispensing feature 106, such as a nozzle or opening, which is associated with the housing 102. For example, the nozzle or opening may have a small diameter, such that the device is capable of delivering a thin stream or small droplets of the fluid at a high velocity.

In certain embodiments, as shown in FIGS. 2, 3, 4, and 5A-5C, the fluid dispensing system 201, 301, 401, 501 of the device includes at least one reservoir 220, 320, 420, 538 associated with the housing 202, 302, 402, 502 and configured to contain a fluid, and a fluid dispensing mechanism disposed within the housing 202, 302, 402, 502 and configured to dispense the fluid from the at least one reservoir 220, 320, 420, 538 past the cervix (shown as 534 in FIGS. 5A-5C) and to the uterus of the subject. Various fluid dispensing mechanisms may be utilized in these devices, some of which are discussed herein. Other suitable fluid dispensing mechanisms known to those of ordinary skill in the art, or modified versions of the fluid dispensing mechanisms disclosed herein, may also be utilized.

In certain embodiments, the fluid dispensing mechanism is an inkjet or other high-velocity fluid dispensing mechanism. For example, a thermal bubble or piezoelectric-type inkjet dispensing mechanism may be utilized. These mechanisms may advantageously propel the fluid out of the device at a high velocity such that the fluid is likely to penetrate, or pass, the cervix of the subject.

Figure 2:
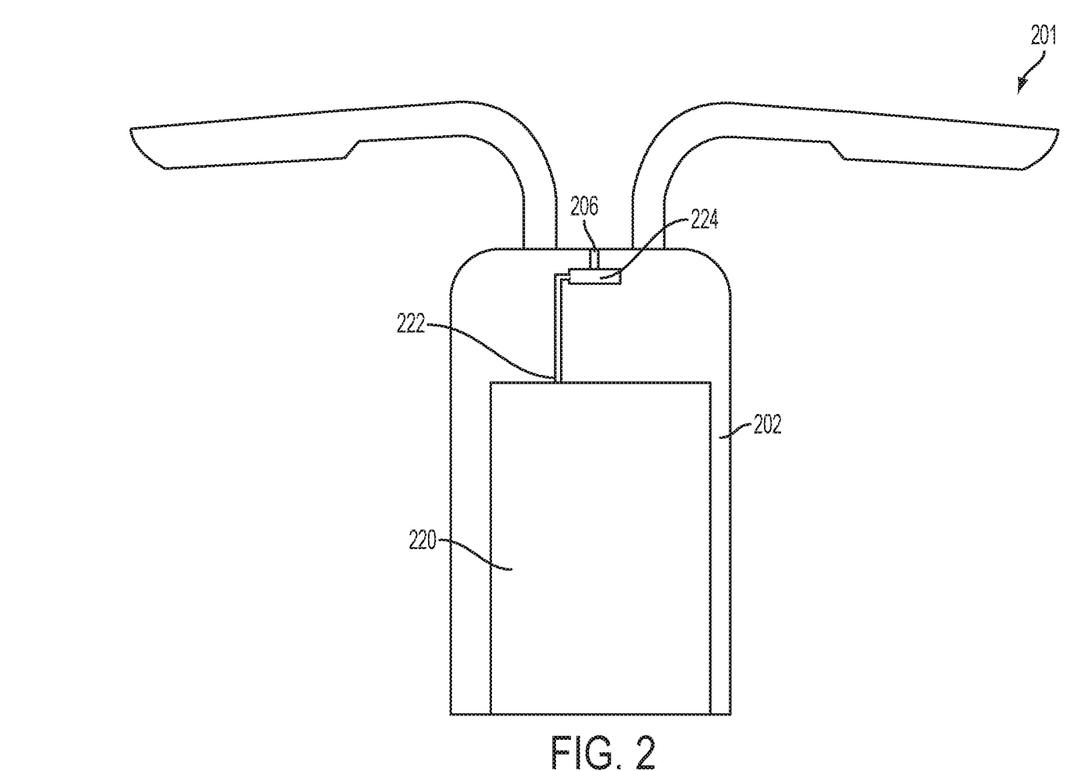
FIG. 2 is a partial cross-sectional view of one embodiment of an implantable fluid delivery device.

In one embodiment, as shown in FIG. 2, the fluid dispensing mechanism is a thermal bubble jet mechanism, which includes a bubble jet chamber 224 in fluid communication with the at least one reservoir 220, and a nozzle 206 in fluid communication with the bubble jet chamber 224. For example, the bubble jet chamber 224 may be connected to the reservoir 220 by a channel 222 or other suitable connection means. In the embodiment shown in FIG. 2, the thermal bubble jet mechanism is configured to generate heat in the bubble jet chamber 224 and thereby create a bubble of the fluid such that a droplet of the fluid is dispensed via the nozzle 206 upon expansion of the bubble.

In one embodiment, the thermal bubble jet mechanism is configured to generate heat in the bubble jet chamber via one or more resistors. In one embodiment, the thermal bubble jet mechanism is configured to generate a vacuum in the bubble jet chamber 224 such that fluid in the at least one reservoir 220 is drawn into the bubble jet chamber 224 upon collapse of the bubble.

Figure 3:
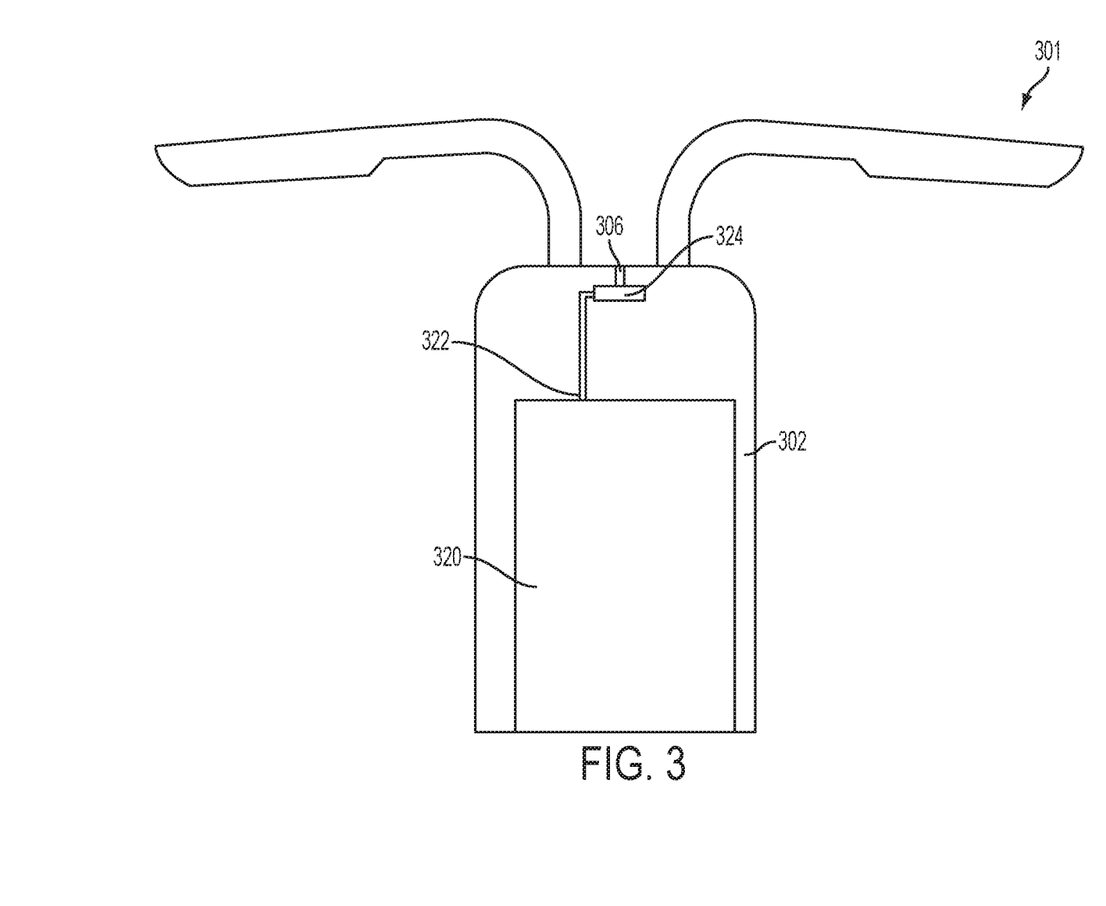
FIG. 3 is a partial cross-sectional view of another embodiment of an implantable fluid delivery device.

In one embodiment, as shown in FIG. 3, the fluid dispensing mechanism comprises a piezoelectric jet mechanism, which includes a jet chamber 324 in fluid communication with the at least one reservoir 320. For example, the jet chamber 324 may be connected to the reservoir 320 by a channel 322 or other suitable connection means. The fluid dispensing mechanism shown in FIG. 3 also includes a piezoelectric material in communication with the jet chamber 324 and a nozzle 306 in fluid communication with the jet chamber 324. The piezoelectric material is configured to receive an electric charge causing it to vibrate and thereby drive fluid in the jet chamber 324 therefrom such that the fluid is dispensed via the nozzle 306.

In one embodiment, the piezoelectric jet mechanism is configured to generate a vacuum in the jet chamber 324 such that fluid from the at least one reservoir 320 is drawn into the jet chamber 324 upon dispense of fluid via the nozzle 306.

Figure 4:
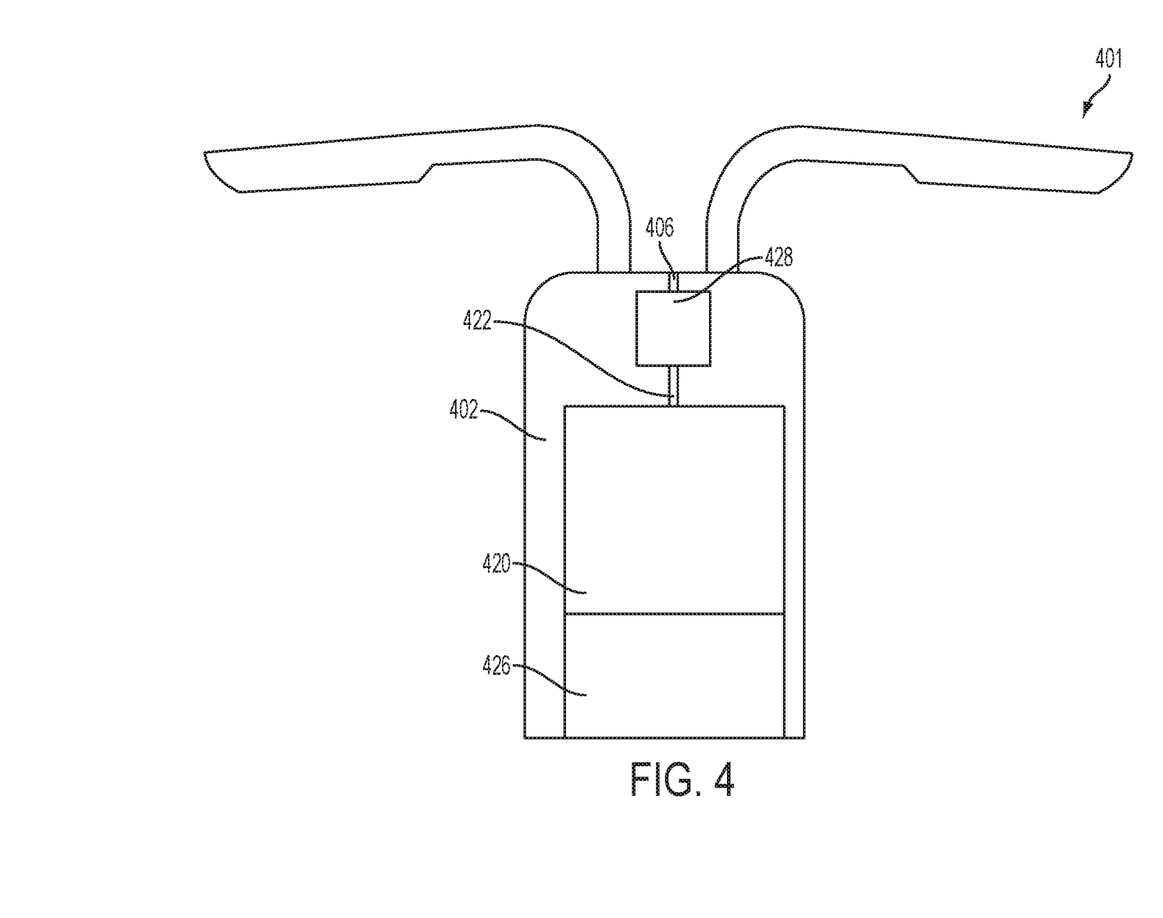
FIG. 4 is a partial cross-sectional view of yet another embodiment of an implantable fluid delivery device.

In one embodiment, as shown in FIG. 4, the fluid dispensing mechanism includes a high velocity pump, which includes a valve 428 configured to selectively allow flow of the fluid from the at least one reservoir 420 to a nozzle 406 and a pressure source 426 configured to drive the fluid from the at least one reservoir 420 toward the nozzle 406. In one embodiment, the valve 428 is configured to allow flow of the fluid from the at least one reservoir 420 to the nozzle 406 upon generation of a sufficient pressure in the at least one reservoir 420 via the pressure source 426, such that the fluid is dispensed via the nozzle 406. As used herein, the term "sufficient pressure" refers to a pressure that is great enough to drive the fluid from the intravaginally deployed device, past the cervix to the uterus of the subject.

For example, the nozzle 406 may be connected to the reservoir 420 by a channel 422 or other suitable connection means, at which a valve may be located to regulate flow of the fluid to the nozzle. For example, the valve may be actuated by electronics on board the device, such as the controller of the control system.

In one embodiment, the pressure source includes compressed gases, springs, pistons, or combinations thereof. For example, the pressure source may include, or be associated with, an actuation mechanism 108 of a control system 114, as shown in FIG. 1B.

Figure 5A:
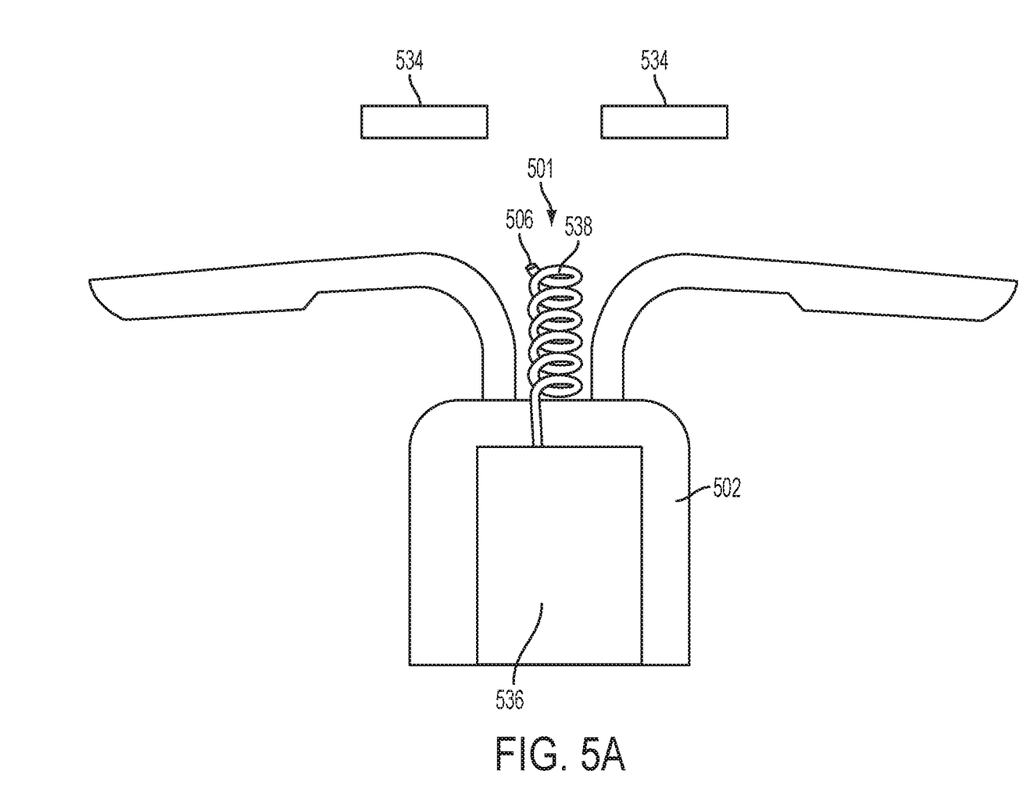
FIG. 5A is a partial cross-sectional view of yet another embodiment of an implantable fluid delivery device having an extending member, shown in the unstressed position.
Figure 5B:
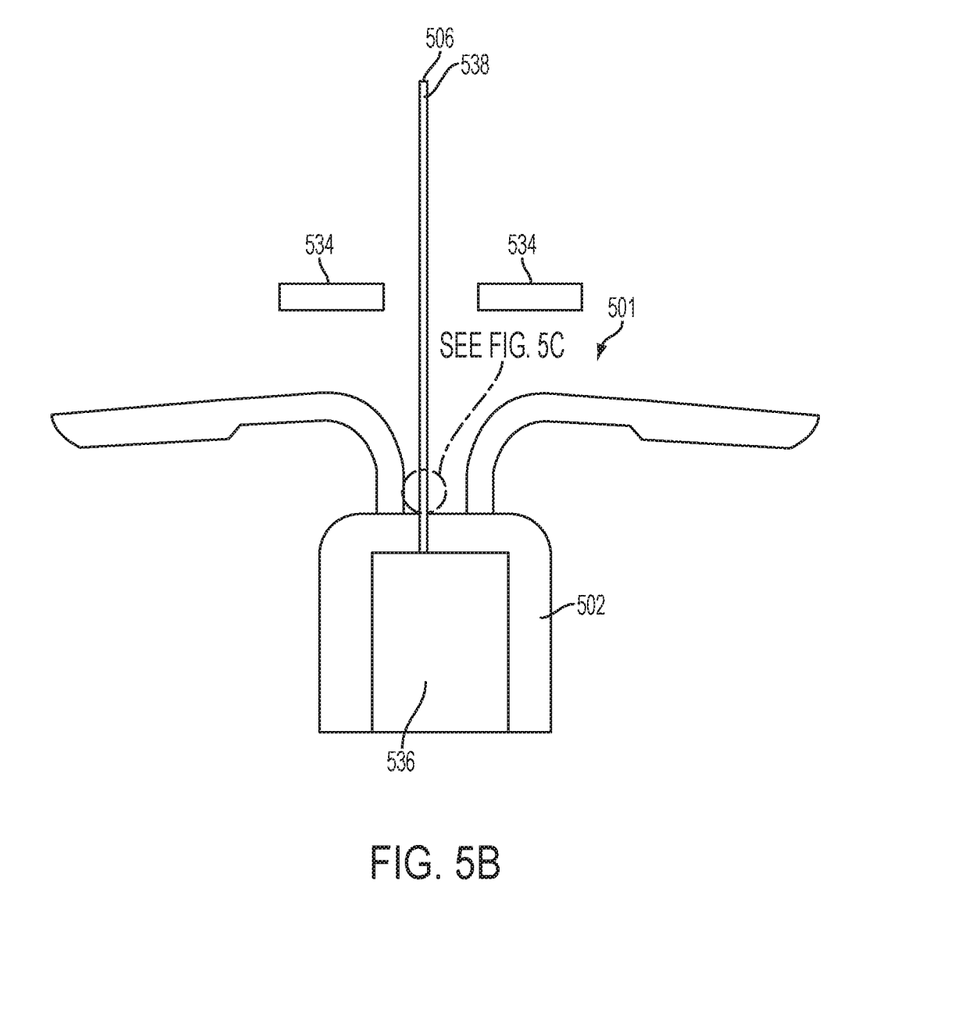
FIG. 5B is a partial cross-sectional view of the implantable fluid delivery device of FIG. 5A, showing the extending member in the extended position.
Figure 5C:
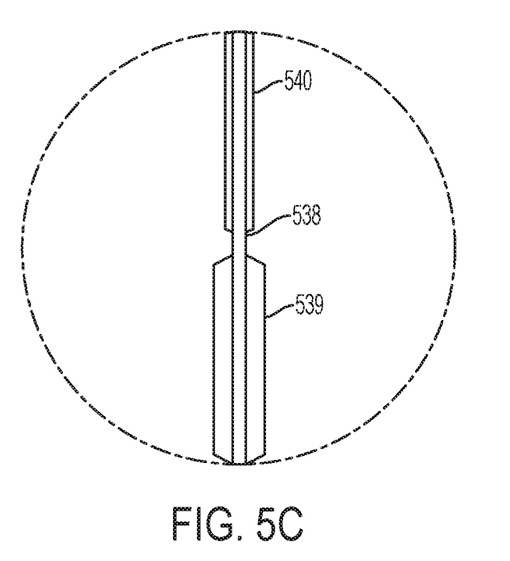
FIG. 5C is a magnified partial cross-sectional view of the implantable fluid delivery device of FIG. 5B.

In one embodiment, as shown in FIGS. 5A-5C, the at least one reservoir includes a tube 538 extending from a gas reservoir 536 of the device, and which includes at least one gas chamber 539, 540 configured to receive gas from the gas reservoir 536 to inflate and thereby urge the tube 538 into an extended position (shown in FIG. 5B). In one embodiment, the at least one gas chamber 539, 540 of the tube 538 is in fluid communication with the fluid contained in the tube such that as the gas chamber 539, 540 inflates, the fluid is driven out of the tube 538.

For example, the tube may include an end nozzle 506 via which the fluid is dispensed from the tube 538. In certain embodiments, the fluid has a surface tension within the tube such that the fluid is not dispensed from the open end of the tube until a sufficient pressure from the inflation of the gas chamber(s) is applied thereto. Alternatively, the end of the tube may include a barrier structure, such as an end cap or seal, configured to maintain the fluid inside the tube until a sufficient pressure from the inflation of the gas chamber(s) ruptures, disengages, or otherwise removes, the barrier structure, such that the fluid can be dispensed.

In one embodiment, as shown in FIG. 5B, the tube 538 is sized to extend past the cervix 534 of the subject in the extended position. That is, the tube 538 may be designed to have a length that extends from the intended vaginal implantation site past the cervix of the subject in which the device is to be implanted. In one embodiment, as shown in FIGS. 5A and 5B, the tube 538 is configured to have a coiled unstressed position and the extended position is an uncoiled position. For example, each of the chambers may be inflated as gas is released from the gas reservoir and the chamber(s) expand thereby forcing the tubing to uncoil. The gas released from the gas reservoir may also serve to drive the fluid from the tube during or upon uncoiling of the tube.

For example, in devices having the extendable tube dispensing mechanism, the velocity of the fluid being dispensed may be lower than that of fluid being dispensed from a device without such an extension tube, because the fluid is being dispensed past the cervix.

In certain embodiments, the tube may be coated with an anti-microbial or anti-wetting coating to prevent contaminants from flowing into the tube from the vaginal or uterine deployment site, or from one gas chamber to another.

In one embodiment, the tube includes at least two gas chambers in series along the tube that have a seal therebetween, such that the second gas chamber may only begin to inflate upon full or near full inflation of the first gas chamber of the tube.

In certain embodiments, a dispense tube is combined with the inkjet-type or high-velocity dispense devices described above. That is, a tube extending between the device and the cervix or uterus of a subject may be provided, either independently of the device (e.g., the tube may be inserted into the subject prior to deployment of the device) or in association with the device (e.g., in connection with the dispensing nozzle or outlet of the device), to ensure delivery of the fluid to the desired site, such as the uterus. Incorporation of such a tube into the device or system may decrease the required fluid velocity produced by the dispensing mechanism, because the fluid is dispensed past the cervix via the tube. In certain embodiments, the tube may be coated with an anti-microbial or anti-wetting coating to prevent contaminants from flowing into the tube from the vaginal or uterine deployment site.

Figure 6:
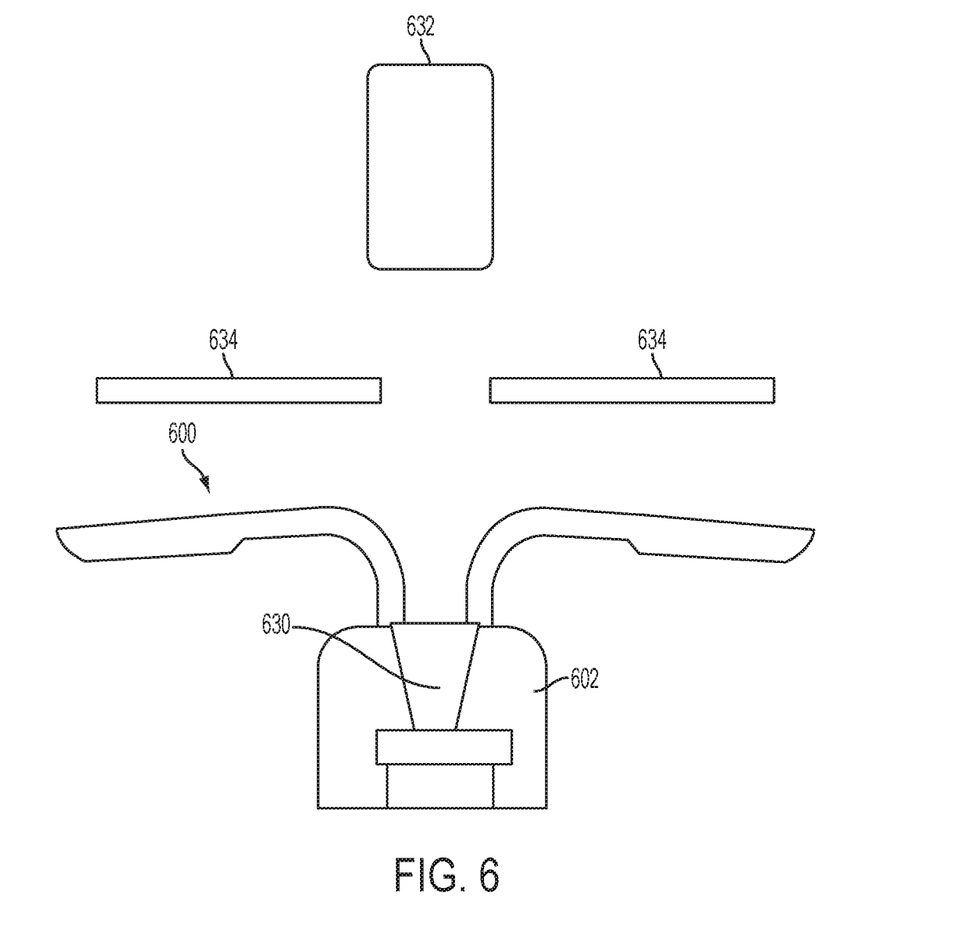
FIG. 6 is a partial cross-sectional view of one embodiment of an implantable fluid delivery system.

In one embodiment, as shown in FIG. 6, an implantable fluid delivery system includes a device 600 having a housing 602 configured for intravaginal deployment and retention in a subject and a fluid dispensing mechanism 630 disposed within the housing 602. The device may include any of the features, or combinations of features, described herein. The system also includes a capsule 632 containing a fluid to be delivered to the subject, the capsule 632 being configured to be inserted past the cervix 632 of the subject prior to deployment of the device 600. In one embodiment, the fluid dispensing mechanism 630 includes an ultrasonic element configured to generate an ultrasonic wave effective to rupture the capsule 632 and release the fluid to the uterus of the subject. For example, the capsule may be inserted past the cervix of the subject manually, for example by ranch personnel in the case of cattle, or using a deployment device configured to deploy the capsule past the cervix.

In one embodiment, the ultrasonic element comprises a piezoelectric material and an acoustic horn.

Suitable device features, including housing designs, retention features, retrieval members, control system features, and additional fluid dispensing mechanisms (not configured for uteral delivery from an intravaginal device), are disclosed in application Ser. No. 13/629,124, filed on Sep. 27, 2012, entitled "Single Channel, Multiple Drug Delivery Device and Methods", application Ser. No. 13/629,159, filed on Sep. 27, 2012, entitled "Multiple Reservoir Drug Delivery Device and Methods", application Ser. No. 13/629,184, filed on Sep. 27, 2012, entitled "Drug Reconstitution and Delivery Device and Methods", application Ser. No. 13/742,203, filed on Jan. 15, 2013, entitled "Devices and Methods for Intraluminal Retention and Drug Delivery", application Ser. No. 14/071,929, filed on Nov. 5, 2013, entitled "Fluid Delivery Devices and Methods", and application Ser. No. 14/107,367, filed on Dec. 16, 2013, entitled "Electrolytic Gas Generating Devices, Actuators, and Methods", each of which is incorporated herein by reference in its entirety.

Advantageously, the devices and systems described herein provide for fluid dispensing to a site past the cervix, with a vaginally implanted device, thereby increasing the precision of the fluid delivery and the likelihood of delivery to the uterus. Desirably, in IVF procedures, these devices and systems increase the efficiency and the likelihood of success of procedures, requiring less time and sperm per subject.

In certain embodiments, the devices described herein may be configured to dispense the fluid when an estrus condition of the subject detected by the device meets a predetermined threshold. That is, the device may be configured to detect when the subject is displaying ideal or near ideal insemination conditions (i.e., estrus) and to dispense the fluid in response to the detection of estrus. Devices for detecting estrus are described in more detail in co-pending application Ser. No. 14/448,074, filed on Jul. 31, 2014, entitled "Implantable Estrus Detection Devices, Systems, and Methods," which is incorporated herein by reference in its entirety.

In certain embodiments, the fluid includes drugs, semen, ova, or combinations thereof.

In certain embodiments, the fluid delivery devices disclosed herein may be configured to release two or more fluids therefrom, such as from separate reservoirs. For example, a device may be configured to dispense a series of drugs to the patient. For example, a device may be configured to dispense both an ova and semen to a patient.

Methods of Fluid Delivery

In another aspect, methods of delivering fluid to a subject are provided. For example, the methods may include deploying a fluid delivery device or system, such as those disclosed herein, in the subject. The devices and systems may include any features, or combinations of features, disclosed herein.

In one embodiment, a method of delivering fluid to a subject includes intravaginally deploying and retaining a device in the subject, and dispensing the fluid from the device such that the fluid is driven past the cervix to the uterus of the subject. For example, the device may include at least one reservoir containing a fluid and a fluid dispensing mechanism.

In one embodiment, dispensing the fluid from the device includes heating a portion of the fluid in a chamber to create a bubble such that a droplet of the fluid is dispensed via a nozzle upon expansion of the bubble.

In one embodiment, dispensing the fluid from the device includes providing an electric charge to a piezoelectric material, thereby causing it to vibrate and drive a portion of the fluid from a chamber such that the portion of fluid is dispensed from the device through a nozzle.

In one embodiment, dispensing the fluid from the device includes generating pressure in the at least one reservoir to drive the fluid toward a nozzle, and the device also includes a valve configured to allow flow of the fluid from the at least one reservoir to the nozzle upon generation of sufficient pressure in the at least one reservoir. For example, the pressure source may include compressed gases, a springs, pistons, and combinations thereof.

In one embodiment, the at least one reservoir includes a tube extending from a gas reservoir of the device, which includes at least one gas chamber that is in fluid communication with the fluid contained in the tube, and the step of dispensing the fluid from the device includes inflating the at least one gas chamber of the tube with gas from a gas reservoir of the device, thereby urging the tube into an extended position and driving the fluid from the tube. For example, the tube may be sized to extend past the cervix of the subject in the extended position. In one embodiment, the tube is configured to have a coiled unstressed position, and the extended position is an uncoiled position.

In certain embodiments, a method of delivering fluid to a subject includes inserting a capsule containing a fluid to be delivered to the subject past the cervix of the subject, thereafter intravaginally deploying a device in the subject, the device comprising a fluid dispensing mechanism, which comprises an ultrasonic element, and generating an ultrasonic wave, via the ultrasonic element, effective to rupture the capsule and release the fluid to the uterus of the subject. In one embodiment, the ultrasonic element includes a piezoelectric material and an acoustic horn.

In one embodiment, dispensing the fluid from the device such that the fluid is driven past the cervix to the uterus of the subject occurs after an estrus condition of the subject detected by the device meets a predetermined threshold. For example, the fluid may include drugs, semen, ova, and combinations thereof. In a particular embodiment, the subject is a horse, cow, sheep, or sow. In another embodiment, the subject is a woman.

It will be appreciated that variants of the above-disclosed and other features and functions, or alternatives thereof, may be combined into many other different devices, systems, methods, or applications. Various presently unforeseen or unanticipated alternatives, modifications, variations, or improvements therein may be subsequently made by those skilled in the art which are also intended to be encompassed by the following claims

We claim:

1. An implantable fluid delivery device, comprising:
   a housing configured for intravaginal deployment and retention in a subject;
   at least one reservoir associated with the housing and configured to contain a fluid; and
   a fluid dispensing mechanism disposed within the housing and configured to dispense the fluid from the at least one reservoir past the cervix and to the uterus of the subject.

2. The device of claim 1, wherein the fluid dispensing mechanism comprises a thermal bubble jet mechanism, which comprises:
   a bubble jet chamber in fluid communication with the at least one reservoir; and
   a nozzle in fluid communication with the bubble jet chamber,
   wherein the thermal bubble jet mechanism is configured to generate heat in the bubble jet chamber and thereby create a bubble of the fluid such that a droplet of the fluid is dispensed via the nozzle upon expansion of the bubble.

3. The device of claim 2, wherein the thermal bubble jet mechanism is configured to generate heat in the bubble jet chamber via one or more resistors.

4. The device of claim 2, wherein the thermal bubble jet mechanism is configured to generate a vacuum in the bubble jet chamber such that fluid in the at least one reservoir is drawn into the bubble jet chamber upon collapse of the bubble.

5. The device of claim 1, wherein the fluid dispensing mechanism comprises a piezoelectric jet mechanism, which comprises:
   a jet chamber in fluid communication with the at least one reservoir;
   a piezoelectric material in communication with the jet chamber; and
   a nozzle in fluid communication with the jet chamber,
   wherein the piezoelectric material is configured to receive an electric charge causing it to vibrate and thereby drive fluid in the jet chamber therefrom such that the fluid is dispensed via the nozzle.

6. The device of claim 5, wherein the piezoelectric jet mechanism is configured to generate a vacuum in the jet chamber such that fluid from the at least one reservoir is drawn into the jet chamber upon dispense of fluid via the nozzle.

7. The device of claim 1, wherein the fluid dispensing mechanism comprises a high velocity pump, which comprises:
   a valve configured to selectively allow flow of the fluid from the at least one reservoir to a nozzle; and
   a pressure source configured to drive the fluid from the at least one reservoir toward the nozzle,
   wherein the valve is configured to allow flow of the fluid from the at least one reservoir to the nozzle upon generation of a sufficient pressure in the at least one reservoir via the pressure source, such that the fluid is dispensed via the nozzle.

8. The device of claim 7, wherein the pressure source is selected from the group consisting of compressed gases, springs, pistons, and combinations thereof.

9. The device of claim 1, wherein the device is configured to dispense the fluid when an estrus condition of the subject detected by the device meets a predetermined threshold.

10. The device of claim 1, wherein the fluid is selected from the group consisting of drugs, semen, ova, and combinations thereof.

11. A method of delivering fluid to a subject, comprising:
    intravaginally deploying and retaining a device in the subject, the device comprising at least one reservoir containing a fluid and a fluid dispensing mechanism; and
    dispensing the fluid from the device such that the fluid is driven past the cervix to the uterus of the subject.

12. The method of claim 11, wherein dispensing the fluid from the device comprises heating a portion of the fluid in a chamber to create a bubble such that a droplet of the fluid is dispensed via a nozzle upon expansion of the bubble.

13. The method of claim 11, wherein dispensing the fluid from the device comprises providing an electric charge to a piezoelectric material, thereby causing it to vibrate and drive a portion of the fluid from a chamber such that the portion of fluid is dispensed from the device through a nozzle.

14. The method of claim 11, wherein:
    dispensing the fluid from the device comprises generating pressure in the at least one reservoir to drive the fluid toward a nozzle, and
    the device further comprises a valve configured to allow flow of the fluid from the at least one reservoir to the nozzle upon generation of sufficient pressure in the at least one reservoir.

15. The method of claim 14, wherein the pressure source is selected from the group consisting of compressed gases, springs, pistons, and combinations thereof.

16. The method of claim 11, wherein:
    dispensing the fluid from the device such that the fluid is driven past the cervix to the uterus of the subject occurs after an estrus condition of the subject detected by the device meets a predetermined threshold.

17. The method of claim 11, wherein the fluid is selected from the group consisting of drugs, semen, ova, and combinations thereof.

* * * * *